United States Patent
Chen et al.

(10) Patent No.: US 9,335,270 B2
(45) Date of Patent: May 10, 2016

(54) RAMAN SPECTROSCOPIC DETECTION METHOD FOR DETECTING SAMPLE IN VESSEL

(71) Applicant: Nuctech Company Limited, Haidian District, Beijing (CN)

(72) Inventors: Zhiqiang Chen, Beijing (CN); Ziran Zhao, Beijing (CN); Jianhong Zhang, Beijing (CN); Hongqiu Wang, Beijing (CN); Yumin Yi, Beijing (CN)

(73) Assignee: Nuctech Company Limited, Haidian District, Beijing (CN)

( * ) Notice: Subject to any disclaimer, the term of this patent is extended or adjusted under 35 U.S.C. 154(b) by 0 days.

(21) Appl. No.: 14/576,699

(22) Filed: Dec. 19, 2014

(65) Prior Publication Data
US 2015/0185154 A1 Jul. 2, 2015

(30) Foreign Application Priority Data
Dec. 27, 2013 (CN) .......................... 2013 1 0740974

(51) Int. Cl.
*G01J 3/44* (2006.01)
*G01N 21/65* (2006.01)

(52) U.S. Cl.
CPC ............... *G01N 21/65* (2013.01); *G01J 3/4412* (2013.01); *G01N 2201/06113* (2013.01); *G01N 2201/12* (2013.01)

(58) Field of Classification Search
CPC ............... G01N 21/65; G01N 21/658; G01N 2021/656; G01J 3/44; G01J 3/02
USPC .......................................................... 356/301
See application file for complete search history.

(56) References Cited

U.S. PATENT DOCUMENTS

| | | | | |
|---|---|---|---|---|
| 8,873,041 B1 * | 10/2014 | Chai et al. | ...................... | 356/301 |
| 2001/0034478 A1 * | 10/2001 | Lambert et al. | ............... | 600/318 |
| 2010/0053606 A1 * | 3/2010 | Matousek et al. | ............. | 356/301 |
| 2012/0070362 A1 * | 3/2012 | Harms et al. | .................. | 423/349 |

* cited by examiner

*Primary Examiner* — Tarifur Chowdhury
*Assistant Examiner* — Md M Rahman
(74) *Attorney, Agent, or Firm* — Merchant & Gould P.C.

(57) ABSTRACT

An embodiment of the present invention provides a Raman spectroscopic detection method for detecting a sample in a vessel, comprising the steps of: (a) measuring a Raman spectrum of the vessel to obtain a first Raman spectroscopic signal; (b) measuring a Raman spectrum of the sample through the vessel to obtain a second Raman spectroscopic signal; (c) removing an interference caused by the Raman spectrum of the vessel from the second Raman spectroscopic signal on basis of the first Raman spectroscopic signal to obtain a third Raman spectroscopic signal of the sample itself; and (d) identifying the sample on basis of the third Raman spectroscopic signal. By means of the above method, the Raman spectrum of the sample in the vessel may be detected correctly so as to identify the sample to be detected efficiently.

8 Claims, 6 Drawing Sheets

330 dividing the one or more characterizing intensity values extracted from the second Raman spectroscopic signal by the one or more characterizing intensity values in the first Raman spectroscopic signal to obtain one or more quotients respectively, the one or more characterizing intensity values extracted from the second Raman spectroscopic signal corresponding to the one or more characterizing intensity values in the first Raman spectroscopic signal in positions — 331 selecting the minimum of the quotients as the subtraction coefficient — 332

RAMAN SPECTROSCOPIC DETECTION METHOD FOR DETECTING SAMPLE IN VESSEL

CROSS-REFERENCE TO RELATED APPLICATION

This application claims the benefit of Chinese Patent Application No. 201310740974.9 filed on Dec. 27, 2013 in the State Intellectual Property Office of China, the whole disclosure of which is incorporated herein by reference.

BACKGROUND OF THE INVENTION

1. Field of the Invention

The present disclosure relates to the technical field of Raman spectroscopic detection, and in particular, to a method for detecting a sample in a vessel using Raman spectroscopy.

2. Description of the Related Art

Raman spectrum is a molecule vibration spectrum, which may reflect fingerprints of molecules and may be used for detection of a matter. The Raman spectroscopy detects and identifies a matter by detecting Raman spectra produced by Raman scattering effects of an exciting light by an object to be detected. The Raman spectroscopic detection method has been widely applied in fields of such as liquid security inspection, jewel detection, explosive detection, drug detection, medicine detection and the like.

In detection of a matter, there is a challenge for the Raman spectroscopic detection method, that is, to detect a sample in a vessel. As the sample to be detected may need to be contained in the vessel sometimes, even packaged in the vessel, it is inevitable that the detection may be interfered by the vessel, for example package.

SUMMARY OF THE INVENTION

An embodiment of the present invention provides a Raman spectroscopic detection method for detecting a sample in a vessel, comprising the steps of:

(a) measuring a Raman spectrum of the vessel to obtain a first Raman spectroscopic signal;

(b) measuring a Raman spectrum of the sample through the vessel to obtain a second Raman spectroscopic signal;

(c) removing an interference caused by the Raman spectrum of the vessel from the second Raman spectroscopic signal on basis of the first Raman spectroscopic signal to obtain a third Raman spectroscopic signal of the sample itself; and (d) identifying the sample on basis of the third Raman spectroscopic signal.

DETAILED DESCRIPTION OF PREFERRED EMBODIMENTS OF THE INVENTION

Exemplary embodiments of the present invention will be described hereinafter in detail with reference to the attached drawings, wherein the like reference numerals refer to the like elements. The present invention may, however, be embodied in many different forms and should not be construed as being limited to the embodiment set forth herein; rather, these embodiments are provided so that the present invention will be thorough and complete, and will fully convey the concept of the disclosure to those skilled in the art.

When a Raman spectroscopy is used to detect a sample, the sample to be detected often needs to be contained in a vessel, such as a package bottle, a package box, a pot and the like, in particular, in the case where the sample is liquid, gas or powers. Thus, the detection of sample may need to irradiate the sample by an exciting light through the vessel and the vessel may also generate Raman scattering effects for the exciting light. In this way, the vessel may interfere the Raman spectroscopic signal of the sample itself. Elimination of such interference is very important to detect and identify the sample correctly and efficiently.

Figure 1:
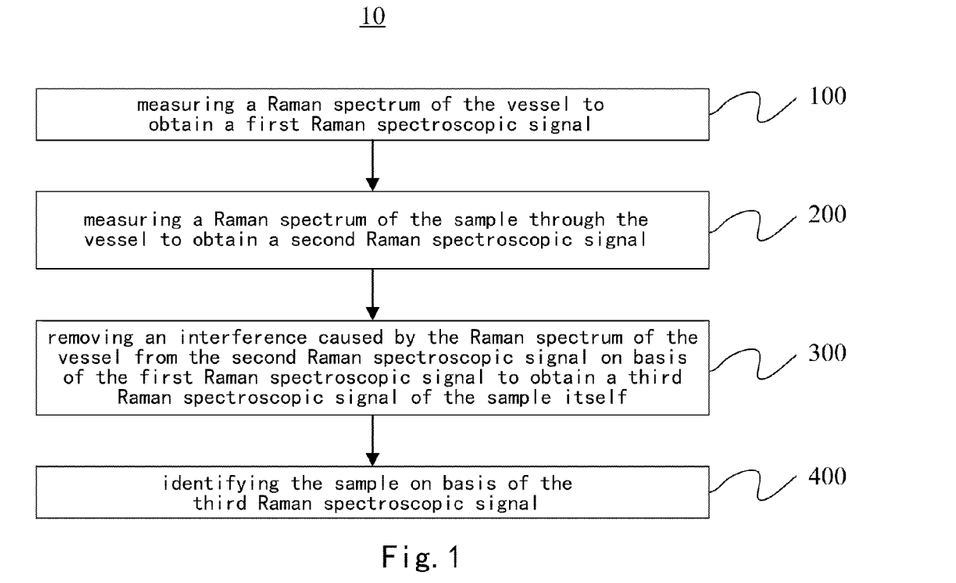
FIG. 1 shows a schematic flow chart of a Raman spectroscopic detection method for detecting a sample in a vessel according to an embodiment of the present invention.

FIG. 1 shows a schematic flow chart of a Raman spectroscopic detection method for detecting the sample in the vessel according to an embodiment of the present invention. The method 10 may include: step 100 of measuring a Raman spectrum of the vessel to obtain a first Raman spectroscopic signal; step 200 of measuring a Raman spectrum of the sample through the vessel to obtain a second Raman spectroscopic signal; step 300 of removing an interference caused by the Raman spectrum of the vessel from the second Raman spectroscopic signal on basis of the first Raman spectroscopic signal to obtain a third Raman spectroscopic signal of the sample itself; and step 400 of identifying the sample on basis of the third Raman spectroscopic signal.

The first Raman spectroscopic signal is the Raman spectroscopic signal of the vessel, which depends on the nature of matter of the vessel. Measuring the Raman spectrum of the vessel may be achieved by focusing an exciting light (such as a laser) onto the vessel so as to obtain the first Raman spectroscopic signal. The second Raman spectroscopic signal may include the Raman spectroscopic signal of the vessel and the Raman spectroscopic signal of the sample itself. Measuring the Raman spectrum of the sample in the vessel may be achieved by focusing the exciting light (such as a laser) onto the sample through the vessel so as to obtain a second Raman spectroscopic signal. If the sample in the vessel is identified directly on basis of the second Raman spectroscopic signal, for example, by comparing it with a reference Raman spectroscopic signal of a target matter, the sample may not be detected correctly due to adverse influence from the vessel.

Therefore, in the Raman spectroscopic detection method according to an embodiment of the present invention, an interference caused by the Raman spectrum of the vessel is removed from the second Raman spectroscopic signal by means of the first Raman spectroscopic signal to obtain a third Raman spectroscopic signal. The third Raman spectroscopic signal is the Raman spectroscopic signal of the sample itself, which may be used to identify and detect the sample in the above step 400. As an example, the step 400 may include identifying the sample by comparing the third Raman spectrum signal with Raman spectrum data in a reference Raman spectrum library. The reference Raman spectrum library may be established previously according to the results of Raman spectroscopic detection of known matters.

The interference caused by the Raman spectrum of the vessel may be removed from the second Raman spectroscopic signal by various methods, for example, comparing the first Raman spectroscopic signal with the second Raman spectroscopic signal directly by plotting points or listing a table or estimating the similarity or interrelation of the first Raman spectroscopic signal and the second Raman spectroscopic signal based on correlation operation and the like. However, these methods are not desired in terms of computation efficiency, and may introduce additional errors.

Figure 2:
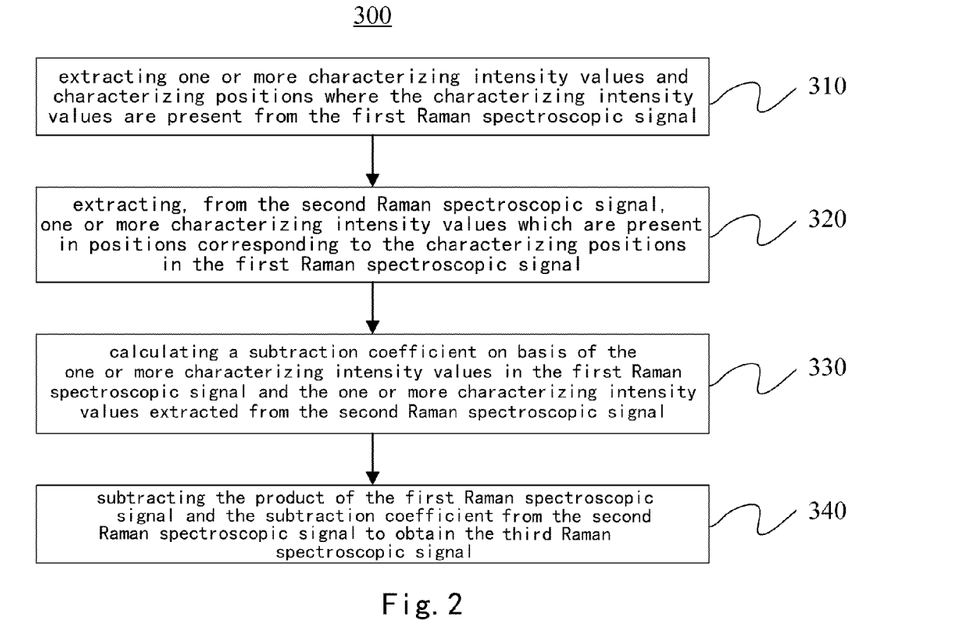
FIG. 2 shows a schematic flow chart of removing an interference caused by the Raman spectrum of the vessel from the second Raman spectroscopic signal on basis of the first Raman spectroscopic signal according to an embodiment of the present invention.

In view of this, an embodiment of the present invention provides a simple and effective method for removing the interference caused by the Raman spectrum of the vessel from the second Raman spectroscopic signal, as illustrated in FIG. 2. As an example, the method may include: step 310 of extracting one or more characterizing intensity values and the characterizing positions where the characterizing intensity values are present from the first Raman spectroscopic signal; step 320 of extracting, from the second Raman spectroscopic signal, one or more characterizing intensity values which are present in positions corresponding to the characterizing positions in the first Raman spectroscopic signal; step 330 of calculating a subtraction coefficient on basis of the one or more characterizing intensity values in the first Raman spectroscopic signal and the one or more characterizing intensity values extracted from the second Raman spectroscopic signal; and step 340 of subtracting the product of the first Raman spectroscopic signal and the subtraction coefficient from the second Raman spectroscopic signal to obtain the third Raman spectroscopic signal.

In order to remove the interference caused by the Raman spectrum of the vessel from the second Raman spectroscopic signal, it at first needs to acquire the characteristic information of the Raman spectrum of the vessel, for example one or more characterizing intensity values in the above step 310, from the first Raman spectroscopic signal. In order to determine the relationship between the first Raman spectroscopic signal and the interference caused by the vessel in the second Raman spectroscopic signal, it further needs to acquire characterizing intensity values, from the second Raman spectroscopic signal, which are present in positions corresponding to the characterizing positions in the first Raman spectroscopic signal. For example, considering the influence of the focal position of the exciting light, the signal intensities produced by the Raman spectrum of the vessel in the first Raman spectroscopic signal and those in the second Raman spectroscopic signal may be different from each other. Thus, when the interference signal caused by the Raman spectrum of the vessel is removed from the second Raman spectroscopic signal, a suitable subtraction coefficient needs to be considered. The subtraction coefficient represents the ratio of the signal intensities produced by the Raman spectrum of the vessel in the second Raman spectroscopic signal to those in the first Raman spectroscopic signal. In calculation of subtraction coefficient, all or part of characterizing intensity values in the first Raman spectroscopic signal may be used, for example, one, two, three, four, five or more characterizing intensity values may be used. The calculation results will be more accurate when all of characterizing intensity values are used.

Figure 3:
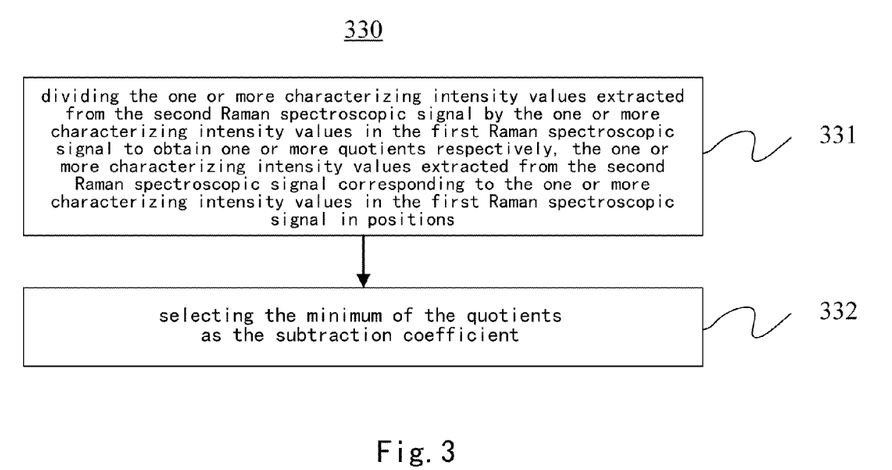
FIG. 3 shows a schematic flow chart of the step of calculating a subtraction coefficient according to an embodiment of the present invention.

In an example, a method for calculating the subtraction coefficient is provided, as illustrated in FIG. 3. The method may include: step 331 of dividing the one or more characterizing intensity values extracted from the second Raman spectroscopic signal by the one or more characterizing intensity values in the first Raman spectroscopic signal to obtain one or more quotients respectively, the one or more characterizing intensity values extracted from the second Raman spectroscopic signal corresponding to the one or more characterizing intensity values in the first Raman spectroscopic signal in positions; and step 332 of selecting the minimum of the quotients as the subtraction coefficient. It should be noted that if there is only one quotient, the minimum of the quotient will be itself. Such method may effectively avoid attenuations of the characterizing intensity values in the Raman spectroscopic signal of the sample to be detected in removing the interference caused by the Raman spectrum of the vessel.

Since the characteristics of the Raman spectroscopic signal are mainly the positions and intensities of characterizing peaks, the above characterizing intensity values generally are intensity values of characterizing peaks, i.e., peak intensity values of the Raman spectroscopic signal. However, it is not limited, for example, the above characterizing intensity values may alternatively be certain values on a slope of the characterizing peaks, inflection points of phase, and the like.

The above method for calculating the subtraction coefficient is advantageous in particular if part of characterizing peaks in the Raman spectrum of the sample to be detected overlaps the characterizing peaks in the Raman spectroscopic signal of the vessel in positions. The characterizing intensity values of the first Raman spectrum signal only reflect the contribution of the Raman scattering of the vessel while the characterizing intensity values of the second Raman spectrum signal reflect both the contribution of the Raman scattering of the vessel and the contribution of the Raman scattering of the sample to be detected. Therefore, the greater quotients mean greater contribution of the Raman scattering of the sample at the position to the second Raman spectroscopic signal, and often mean the overlapping of the characterizing portions (for example characterizing peaks) in the Raman spectrum of the vessel with the characterizing portions (for example characterizing peaks) in the Raman spectrum of the sample to be detected becomes more significant or the characterizing intensity values of the Raman spectrum of the sample to be detected become larger at the position, and vice versa. Selecting minimum quotient as the subtraction coefficient may prevent the characterizing intensity values of the sample to be detected from being reduced upon removing the interference caused by the Raman spectrum of the vessel. It may be helpful for ensuring accuracy of final recognition of the sample to be detected.

Meanwhile, for the case that all of characterizing peaks in the Raman spectrum of the sample to be detected are overlapped with the characterizing peaks in the Raman spectroscopic signal of the vessel in position, it is almost not presented due to the principles of Raman scattering. Thus, it will not be considered generally in practice.

Figure 4A:
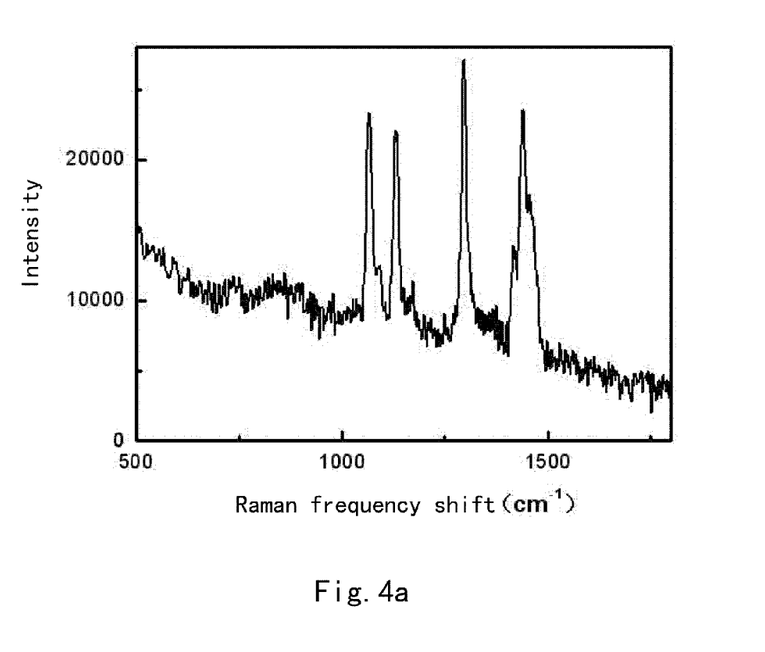
FIGS. 4a-4c show schematically a first Raman spectroscopic signal, a second Raman spectroscopic signal and a third Raman spectroscopic signal in a first detection example using a Raman spectroscopic detection method according to an embodiment of the present invention respectively.
Figure 4B:
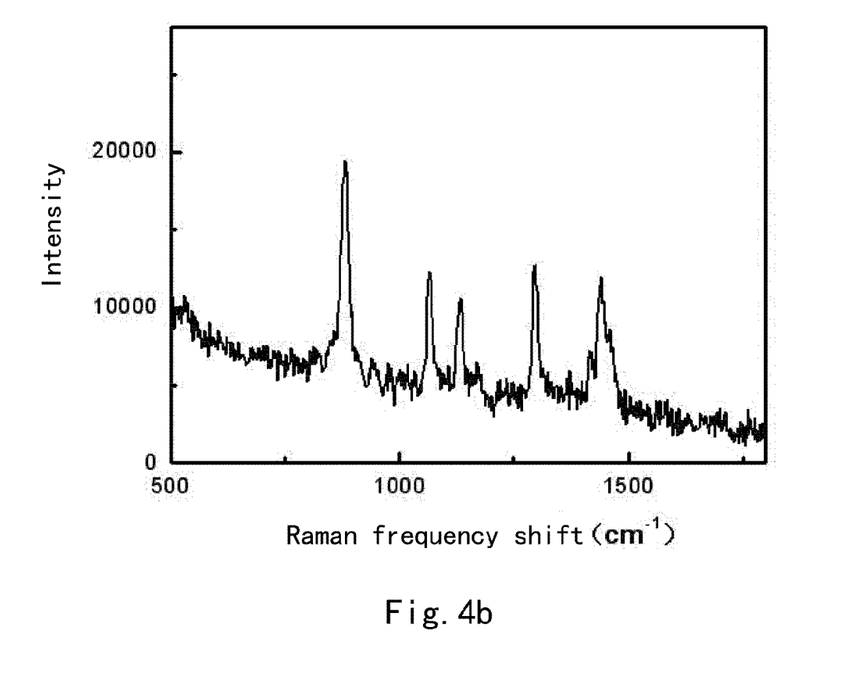
Figure 4C:
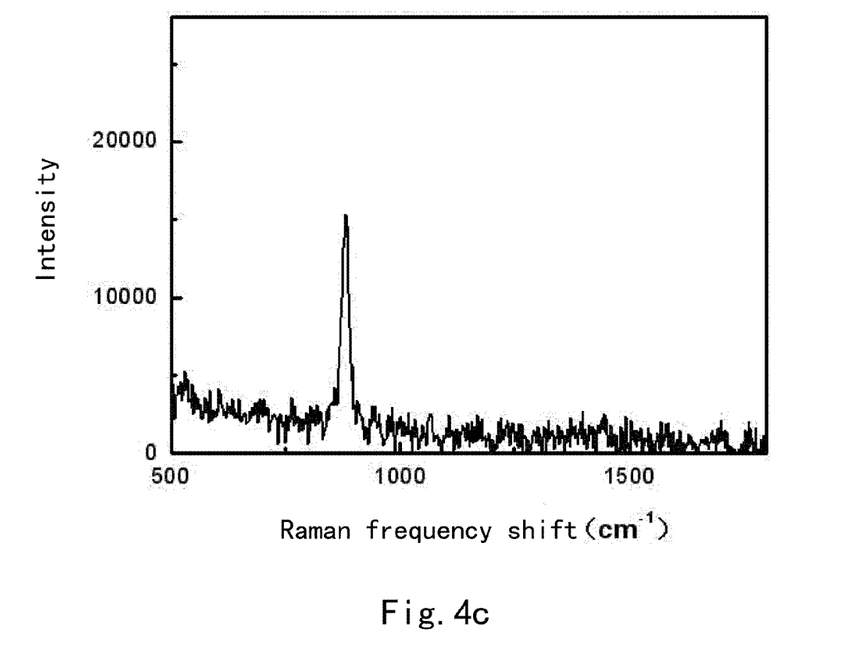

FIGS. 4*a*-4*c* show schematically a first example of a detecting process using a Raman spectroscopic detection method according to an embodiment of the present invention. In the example, the sample to be detected is hydrogen peroxide contained in a high density polyethylene plastic (HDPE) bottle as the vessel.

In detection, an exciting light is focused on the HDPE bottle to acquire the first Raman spectroscopic signal. The acquired first Raman spectroscopic signal is shown in FIG. 4a. In the first Raman spectroscopic signal, the characterizing intensity values and the corresponding characteristic positions are listed in Table 1 (represented as the characterizing intensity value 1 in Table 1). Then, the exciting light is focused on the sample (liquid) in the HDPE bottle to acquire the second Raman spectroscopic signal. The acquired second Raman spectroscopic signal is shown in FIG. 4b. In the second Raman spectroscopic signal, the characterizing intensity values corresponding to the characteristic positions in the first Raman spectroscopic signal are also listed in Table 1 (represented as the characterizing intensity value 2 in Table 1). Then, the above characterizing intensity values in the second Raman spectroscopic signal are divided by those in the first Raman spectroscopic signal to obtain a set of quotients (see Table 1). It can be seen from Table 1 that the quotients have a minimum of 0.411. This minimum of 0.411 is determined as the subtraction coefficient. The product of the first Raman spectroscopic signal and 0.411 is subtracted from the second Raman spectroscopic signal to acquire a third Raman spectroscopic signal, as illustrated in FIG. 4c. Finally, by comparing the third Raman spectroscopic signal with data in the Raman spectrum library, the composition of the sample can be determined as hydrogen peroxide.

TABLE 1

| No. | Characteristic position (cm$^{-1}$) | Characterizing intensity value 1 (pure number) | Characterizing intensity value 2 (pure number) | Quotient |
|---|---|---|---|---|
| 1 | 1058 | 14500 | 7210 | 0.497 |
| 2 | 1130 | 13120 | 5780 | 0.441 |
| 3 | 1259 | 19410 | 7970 | 0.411 |
| 4 | 1438 | 17600 | 7900 | 0.449 |

Figure 5A:
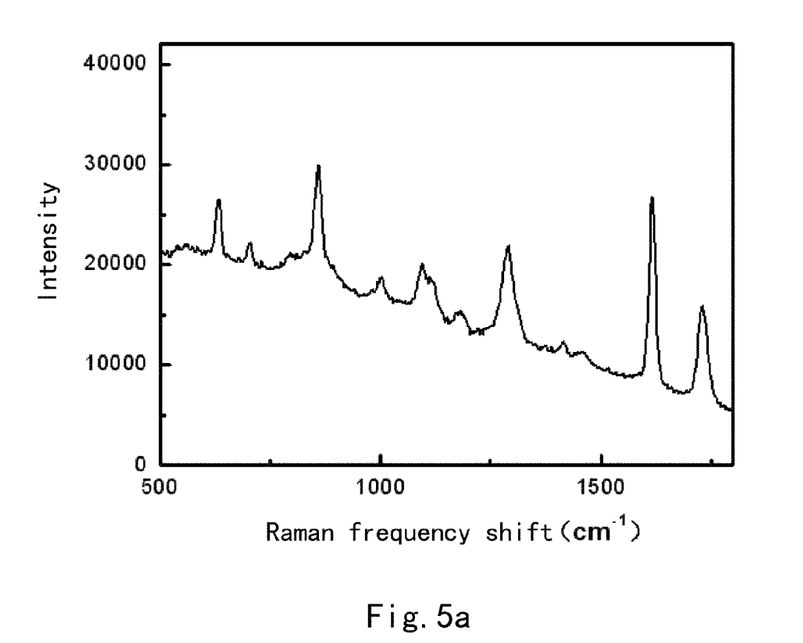
FIGS. 5a-5c show schematically a first Raman spectroscopic signal, a second Raman spectroscopic signal and a third Raman spectroscopic signal in a second detection example using a Raman spectroscopic detection method according to an embodiment of the present invention respectively.
Figure 5B:
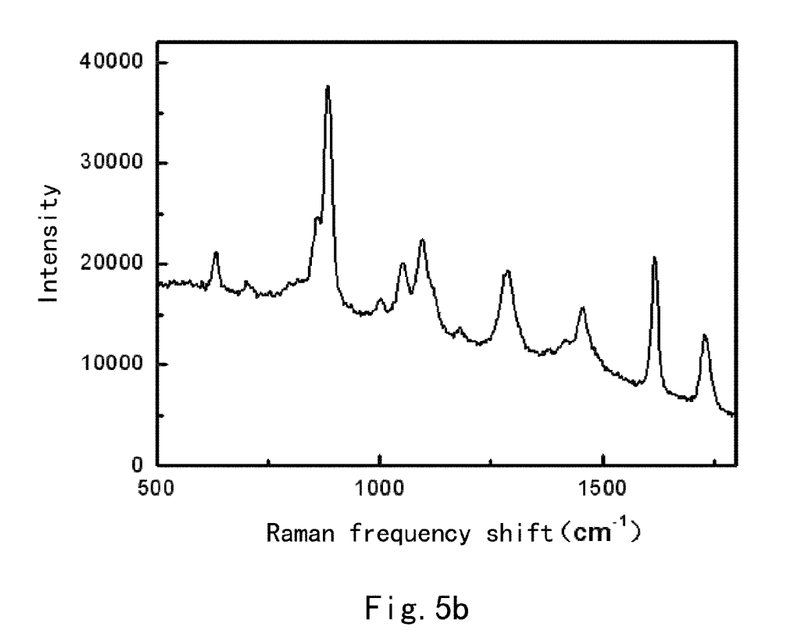
Figure 5C:
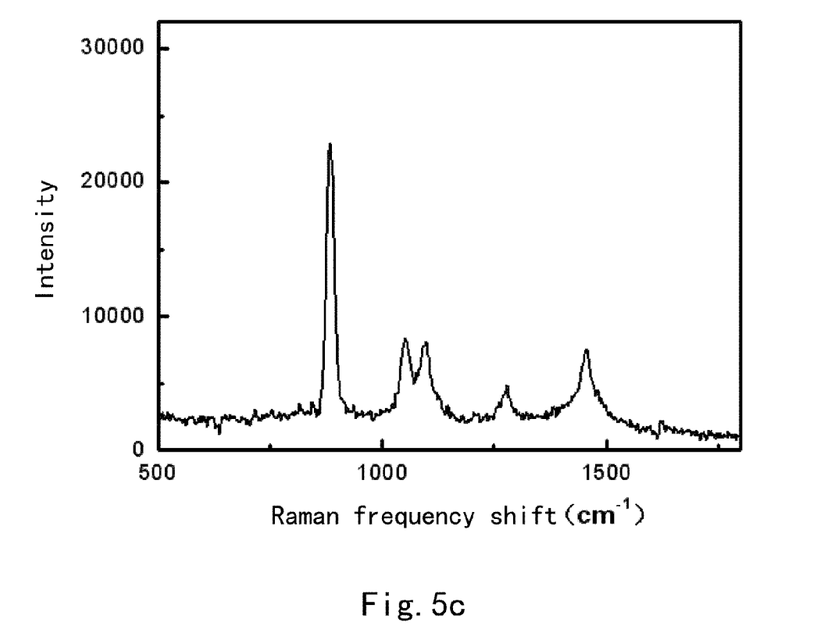

FIGS. 5a-5c show schematically a second example of a detecting process using a Raman spectroscopic detection method according to an embodiment of the present invention. In the example, the sample to be detected is ethanol contained in a poly ethylene terephthalate (PET) bottle as the vessel.

Similar to the above first example, in detection, at first, an exciting light is focused on the PET bottle to acquire the first Raman spectroscopic signal. The acquired first Raman spectroscopic signal is shown in FIG. 5a. Then, the exciting light is focused on the sample (liquid) in the PET bottle to acquire the second Raman spectroscopic signal. The acquired second Raman spectroscopic signal is shown in FIG. 5b. Then, the subtraction coefficient is determined by the above method. And the product of the first Raman spectroscopic signal and the subtraction coefficient is subtracted from the second Raman spectroscopic signal to acquire a third Raman spectroscopic signal, as illustrated in FIG. 5c. Finally, by comparing the third Raman spectroscopic signal with data in the Raman spectrum library, the composition of the sample can be determined as ethanol.

From FIGS. 5a-5c, it can be seen that the Raman spectroscopic signal of the sample (ethanol) has some characterizing peaks overlapping with the characterizing peaks in the Raman spectroscopic signal of the vessel (PET bottle). It is thus understood that the method according to the embodiment of the present invention can still achieve correct measurements even in the case that the Raman spectroscopic signal of the sample has some characterizing peaks overlapping the characterizing peaks in the Raman spectroscopic signal of the vessel.

Figure 6A:
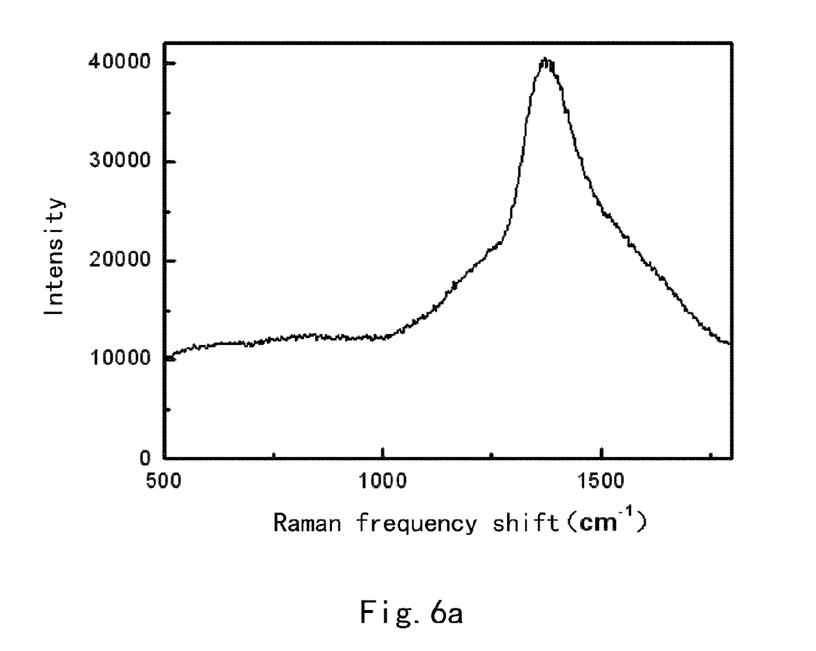
FIGS. 6a-6c show schematically a first Raman spectroscopic signal, a second Raman spectroscopic signal and a third Raman spectroscopic signal in a third detection example using a Raman spectroscopic detection method according to an embodiment of the present invention respectively.
Figure 6B:
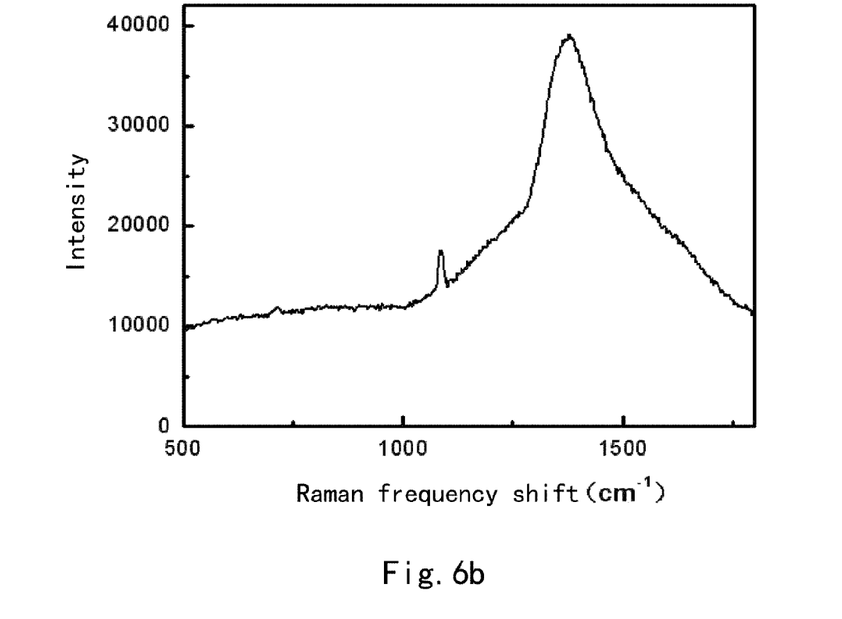
Figure 6C:
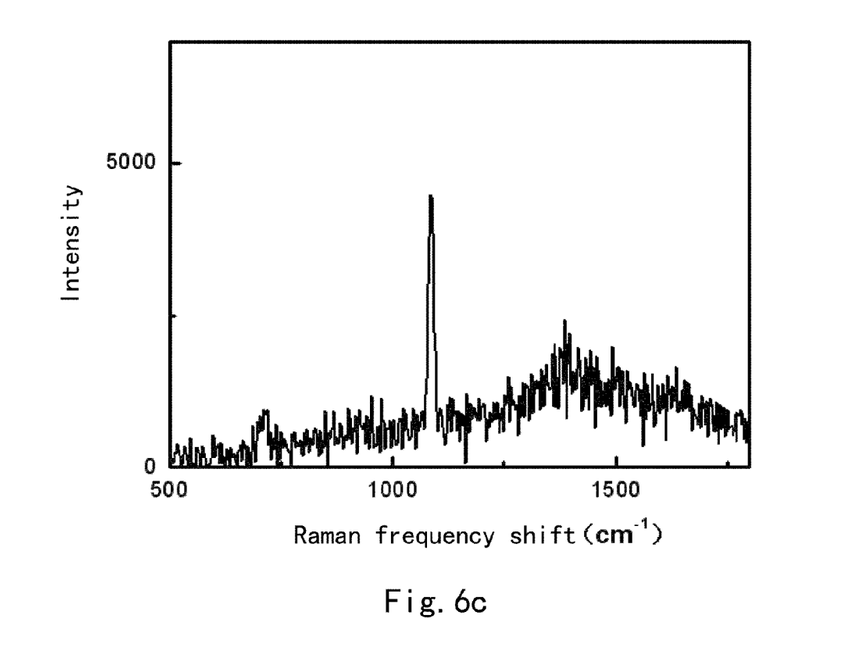

FIGS. 6a-6c show schematically a third example of a detecting process using a Raman spectroscopic detection method according to an embodiment of the present invention. In the example, the sample to be detected is calcium carbonate powers contained in a glass (PET) bottle as the vessel.

Similar to the above two examples, in detection, at first, an exciting light is focused on the glass bottle to acquire the first Raman spectroscopic signal. The acquired first Raman spectroscopic signal is shown in FIG. 6a. Then, the exciting light is focused on the sample (solid) in the glass bottle to acquire the second Raman spectroscopic signal. The acquired second Raman spectroscopic signal is shown in FIG. 6b. Then, the subtraction coefficient is determined by the above method. And the product of the first Raman spectroscopic signal and the subtraction coefficient is subtracted from the second Raman spectroscopic signal to acquire a third Raman spectroscopic signal, as illustrated in FIG. 6c. Finally, by comparing the third Raman spectroscopic signal with data in the Raman spectrum library, the composition of the sample can be determined as calcium carbonate.

From FIGS. 6a-6c, it can be seen that in the second Raman spectroscopic signal, the characterizing peaks in the Raman spectroscopic signal of the sample are almost disappear due to the interference of the Raman spectrum of the vessel (glass bottle). However, the characterizing peaks in the Raman spectroscopic signal of the sample to be detected may still be found correctly to identify the sample correctly and efficiently, by means of the Raman spectroscopic detection method according to the embodiment of the present invention.

Although the present invention has been explained with reference to the drawings, the embodiments shown in the drawings are only illustrative, instead of limiting the present invention.

Although some embodiments of the general inventive concept are illustrated and explained, it would be appreciated by those skilled in the art that modifications and variations may be made in these embodiments without departing from the principles and spirit of the general inventive concept of the disclosure, the scope of which is defined in the appended claims and their equivalents.

What is claimed is:

1. A Raman spectroscopic detection method for detecting a sample in a vessel, comprising the steps of:
    (a) measuring a Raman spectrum of the vessel to obtain a first Raman spectroscopic signal;
    (b) measuring a Raman spectrum of the sample through the vessel to obtain a second Raman spectroscopic signal;
    (c) removing an interference caused by the Raman spectrum of the vessel from the second Raman spectroscopic signal on basis of the first Raman spectroscopic signal to obtain a third Raman spectroscopic signal of the sample itself; and
    (d) identifying the sample on basis of the third Raman spectroscopic signal.

2. The Raman spectroscopic detection method according to claim 1, wherein the step (c) comprises:
    (c1) extracting one or more characterizing intensity values and characterizing positions where the characterizing intensity values are present from the first Raman spectroscopic signal;
    (c2) extracting, from the second Raman spectroscopic signal, one or more characterizing intensity values which are present in positions corresponding to the characterizing positions in the first Raman spectroscopic signal;

(c3) calculating a subtraction coefficient on basis of the one or more characterizing intensity values in the first Raman spectroscopic signal and the one or more characterizing intensity values extracted from the second Raman spectroscopic signal; and (c4) subtracting the product of the first Raman spectroscopic signal and the subtraction coefficient from the second Raman spectroscopic signal to obtain the third Raman spectroscopic signal.

3. The Raman spectroscopic detection method according to claim 2, wherein the step (c3) comprises the following steps of:

(c31) dividing the one or more characterizing intensity values extracted from the second Raman spectroscopic signal by the one or more characterizing intensity values in the first Raman spectroscopic signal to obtain one or more quotients respectively, the one or more characterizing intensity values extracted from the second Raman spectroscopic signal corresponding to the one or more characterizing intensity values in the first Raman spectroscopic signal in positions; and (c32) selecting the minimum of the quotients as the subtraction coefficient.

4. The Raman spectroscopic detection method according to claim 1, wherein the characterizing intensity values are intensity values of characterizing peaks.

5. The Raman spectroscopic detection method according to claim 4, wherein the third Raman spectroscopic signal has some characterizing peaks overlapping with the characterizing peaks in the first Raman spectroscopic signal in positions.

6. The Raman spectroscopic detection method according to claim 1, wherein measuring the Raman spectrum of the vessel is performed by focusing an exciting light onto the vessel, and measuring the Raman spectrum of the sample in the vessel is performed by focusing the exciting light onto the sample through the vessel.

7. The Raman spectroscopic detection method according to claim 1, wherein the vessel is at least partly transparent.

8. The Raman spectroscopic detection method according to claim 1, wherein the step (d) comprises:

identifying the sample by comparing the third Raman spectrum signal with Raman spectrum data in a reference Raman spectrum library.

\* \* \* \* \*